United States Patent [19]
Hurlimann

[11] Patent Number: 6,140,818
[45] Date of Patent: Oct. 31, 2000

[54] NMR LOGGING TOOL AND METHOD FOR FAST LOGGING

[75] Inventor: Martin D. Hurlimann, Ridgefield, Conn.

[73] Assignee: Schlumberger Technology Corporation, Ridgefield, Conn.

[21] Appl. No.: 09/174,583

[22] Filed: Oct. 19, 1998

[51] Int. Cl.[7] .................................................. G01V 3/00
[52] U.S. Cl. .......................... 324/303; 324/322; 324/318
[58] Field of Search .................................. 324/303, 300, 324/306, 322, 318

[56] References Cited

U.S. PATENT DOCUMENTS

| | | | |
|---|---|---|---|
| 4,710,713 | 12/1987 | Strikman | 324/303 |
| 4,933,638 | 6/1990 | Kenyon et al. | 324/303 |
| 5,055,787 | 10/1991 | Kleinberg | 324/303 |
| 5,486,762 | 1/1996 | Freedman et al. | 324/303 |

OTHER PUBLICATIONS

J. M. Singer, L. Johnson, R.L. Kleinberg, and C. Flaum, *Fast NMR Logging for Bound Fluid and Permeability Logging*, presented at SPWLA Annual Logging Symposium, 1997.

*Primary Examiner*—Christine K. Oda
*Assistant Examiner*—Brij B. Shrivastav
*Attorney, Agent, or Firm*—William B. Batzer

[57] ABSTRACT

A high speed, NMR, porosity measuring technique and instrument, is described. The instrument is configured with a long prepolarization region of up to approximately six feet disposed ahead of a short detection region of about six inches. The prepolarization region comprises permanent magnets. The detection region comprises homogeneous magnets and rf antenna. This tool design makes possible the acquisition of NMR porosity measurements at 1800 ft./hr., or more, with wait times between successive detection measurements of approximately one second.

14 Claims, 3 Drawing Sheets

6,140,818

NMR LOGGING TOOL AND METHOD FOR FAST LOGGING

FIELD OF THE INVENTION

The present invention relates to Nuclear Magnetic Resonance (NMR) tools and methods used for well logging, and more particularly, to an NMR instrument and technique having greater logging speeds than previously achieved. The NMR measurement can be used to determine porosity, bound fluid, pore size distribution, permeability, viscosity and diffusion coefficient of fluids.

BACKGROUND OF THE INVENTION

The use of NMR tools for well logging has proved to be a valuable means of analyzing formation characteristics. One disadvantage of current NMR logging apparatuses is their slow logging speeds. Logging speeds for these instruments are typically in the range of between 200 to 300 ft./hr. One of the main reasons for the slow measurement speed of these instruments, is the inherent wait time between their successive measurements. The antenna receiving the signals must, by necessity, wait for the induced magnetization to reach proper spin levels before the next measurement can be taken. Wait times of as much as eight seconds have been necessary in vuggy carbonate formations, owing to the long $T_1$ relaxation time of the fluids, such as: methane, water, and light oils that are contained in these formations.

Recently, a new NMR logging technique has been able to acquire bound fluid porosity measurements at much faster logging speeds. (See, for example. J. M. Singer, L. Johnson, R. L. Kleinberg, and C. Flaum. *Fast NMR Logging for bound Fluid and Permeability Logging*, presented at the SPWLA Annual Logging Symposium, 1997.) For free fluid porosity measurements, however, this technique requires an additional nuclear log.

The present invention features a new NMR logging tool and method that can be used to measure both bound fluid, and free fluid porosity with a logging speed, which has been successfully tested at up to 4200 ft./hr. The wait times between successive measurements of the new NMR logging technique are in the order of about one second. This shortened wait time is even applicable for formations displaying relaxation times of several seconds.

The invention comprises an NMR instrument that has a long prepolarization region of up to about six feet, and a short antenna length of approximately six inches. This unique tool configuration allows the regions ahead of the antenna to sufficiently polarize despite the higher tool speed, such that measurements can be taken in quick succession.

For a given logging speed, v, the wait time $T_w$ between measurements is chosen in such a way that the sensitive regions of two subsequent measurements are not overlapping. Since the sensitive region along the tool direction is typically of the order of the length of the antenna, $L_{antenna}$, or slightly longer, the logging tool should move about an antenna length during the wait time $T_w$. Therefore, the wait time should be approximately $T_w = L_{antenna}/v$. This ensures that the NMR measurement is not affected by the previous measurement.

For logging tools that can be operated at different rf frequencies (see for example patent by Strikman et al., U.S. Pat. No. 4,710,713), measurements at different rf frequencies can be interleaved. As long as the rf frequencies differ by more than the nutation frequency $\gamma B_1$, the sensitive zones for the different rf frequencies are not overlapping. Here $\gamma$ is the gyromagnetic ratio and $B_1$ is the strength of the rf field in the formation. For any given rf frequency, the wait time between measurements should be $T_w = L_{antenna}/v$, but measurements at different rf frequencies can be performed during this time without causing any interference.

As long as the measurements are non-overlapping, the initial amplitude of the CPMG sequence does not depend on the wait time. Note that this is true even if the longitudinal relaxation time, $T_1$, is longer than the wait time $T_w$.

The length of the prepolarization region is preferably long compared to $vT_{1,max}$, where $T_{1,max}$ is the longest relaxation time encountered in the formation. Such a prepolarization region assures that all the spins are exposed to the magnetic field of the prepolarizer for a sufficiently long time. This ensures that they are fully polarized by the time they enter the sensitive region where the NMR measurement is performed. Combined with the wait time discussed above, the measured initial NMR echo amplitude is then directly proportional to the porosity times the hydrogen index. With this scheme, fast logging speed is combined with high spatial resolution. At high logging speed, this spatial resolution, given by the antenna length, can be much higher than $vT_1$.

If the length of the prepolarization region is shorter than $vT_{1,max}$ at the highest desired logging speeds (e.g. for practical limitations on length or weight of the tool), a correction will have to be applied to the measurements to obtain the correct porosity for formations with long $T_1$ relaxation times. This correction will depend on $T_1$, the logging speed, and the length and field profile of the prepolarization region. The present disclosure minimizes this correction. The longer the prepolarization region, the smaller the correction. For overlapping measurements (i.e. shorter wait times than discussed above), the correction becomes larger and more complicated, as it now depends also on the wait time used.

If the corrections are significant, the longitudinal relaxation times $T_1$ have to be determined by a combination of non-overlapping measurements and one or several overlapping measurements. This corresponds to a generalized form of multi-wait logging (see for instance U.S. Pat. No. 5,486,762).

One implementation of this configuration would be for an excentric tool, which is applied against the borehole wall. As aforementioned, this tool design would make it possible to acquire NMR porosity at up to 4200 ft./hr. Such a tool would have a maximal resolution of about one foot. This configuration would not affect any of the present NMR applications.

SUMMARY OF THE INVENTION

In accordance with the present invention, there is provided a high speed well logging instrument and method for obtaining NMR porosity measurements. The NMR tool has an extended prepolarization region of up to about six feet, and a short detection region length of approximately six inches. The detection region is adjacent to the extended prepolarization region, and comprises homogeneous magnets and rf antenna. The instrument is optimal with a length of the prepolarization region to be at least two to three times the product of logging speed times the longest $T_1$ encountered in the formation. The optimal wait time between measurements is given by the ratio of antenna length to logging speed; for 1800 ft./hr., $T_{1long}=4$ s, and $L_{antenna}=6"$, we obtain $L_{prepolarize}=4-6$ ft. and $T_{wait}=1$ s. This unique tool configuration allows the regions ahead of the antenna to sufficiently polarize despite higher tool speeds substantially greater than the usual speed today of 300 feet per hour. With the present invention speed of about 1,800 feet per hour, or even double that in some cases, are possible, thus resulting in wait times between successive measurements in said detection region of less than two seconds, and preferably about one second. NMR instruments benefiting from the invention can comprise excentric or centralized tools. A tool with the inventive configuration would have a maximal resolution of about one foot.

It is an object of this invention to provide an improved NMR tool and method for measuring porosity, bound fluid and permeability in a well logging formation.

It is another object of the invention to provide a high speed NMR tool and method for measuring porosity, bound fluid and permeability in a well logging formation; and It is a further object of this invention to provide a high speed NMR tool and method for measuring porosity, bound fluid and permeability in a well logging formation having wait times between measurements not exceeding approximately one second.

BRIEF DESCRIPTION OF THE DRAWINGS

A complete understanding of the present invention may be obtained by reference to the accompanying drawings, when considered in conjunction with the subsequent detailed description, in which:

FIGS. 1a and 1b, respectively, show cross-sectional views of a centralized NMR tool depicted in FIG. 1;

DESCRIPTION OF THE PREFERRED EMBODIMENT

Figure 1:
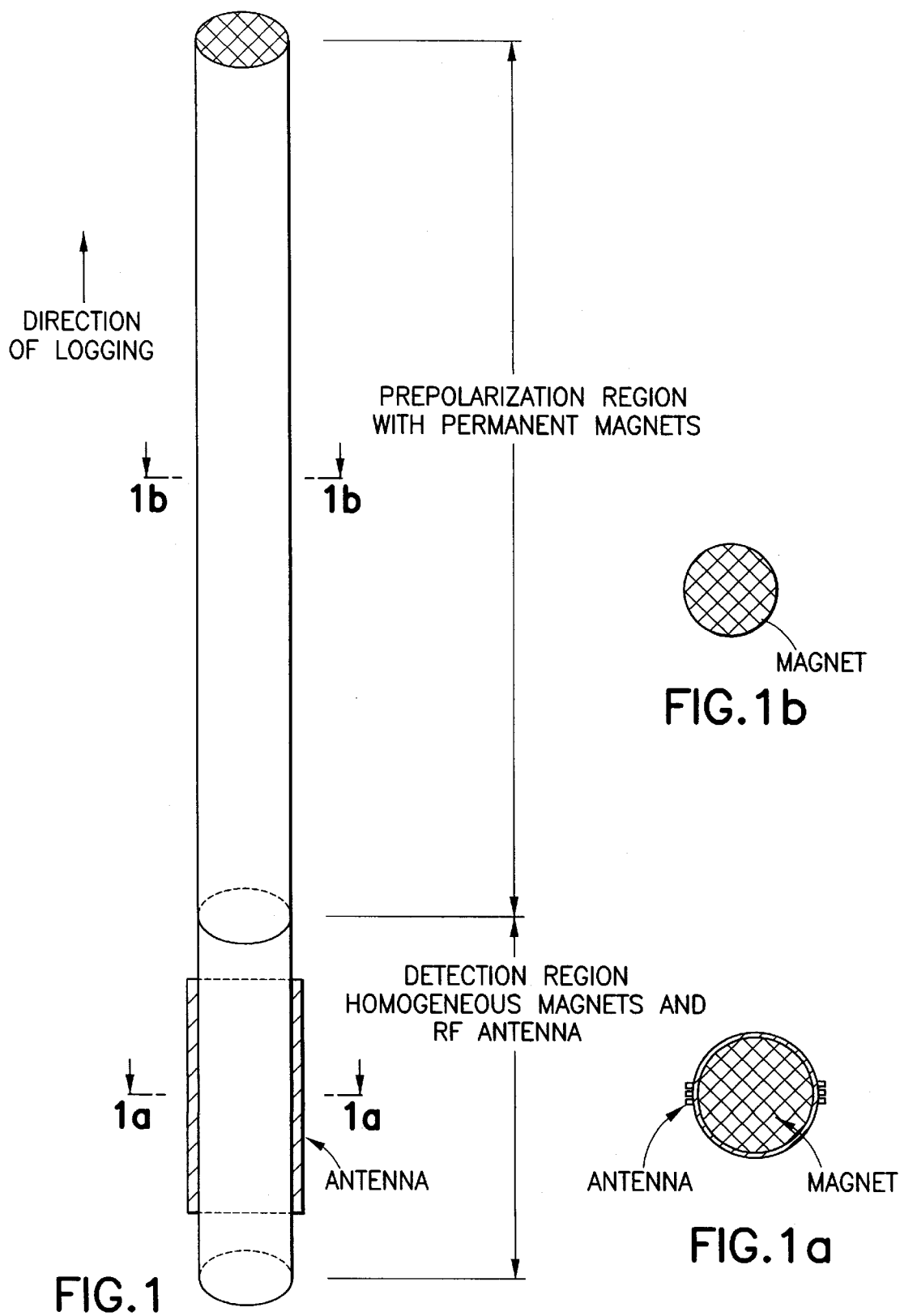
FIG. 1 illustrates a schematic plan view of a centralized NMR tool in accordance with the invention.
Figure 2:
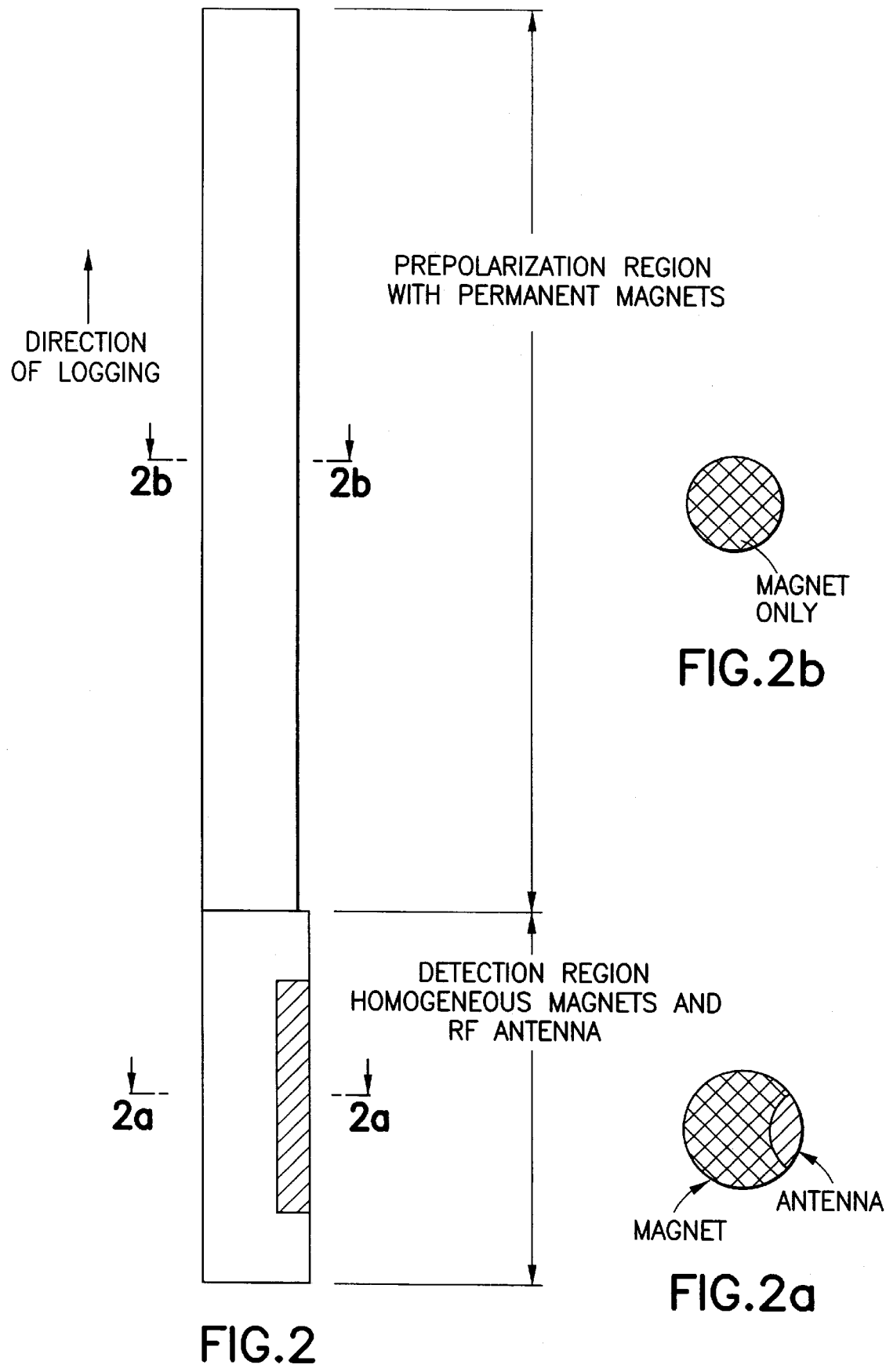
FIG. 2 shows a schematic plan view of an excentric NMR pad tool in accordance with the invention, and FIGS. 2a and 2b, respectively, show cross-sectional views of the tool depicted in FIG. 2.

Generally speaking, the invention features a high speed, NMR measuring technique and instrument. The instrument is configured with a long prepolarization region of up to approximately six feet disposed ahead of a short detection region of about six inches. The prepolarization region comprises permanent magnets. The detection region comprises homogeneous magnets and rf antenna. This tool design makes possible the acquisition of NMR porosity measurements at up to 1800 ft./hr., or even double that speed. The NMR instrument of this invention can comprise a centralized tool, as shown in FIGS. 1, 1a, and 1b. The NMR tool can also comprise a pad-type (excentered) NMR instrument, as shown in FIGS. 2, 2a, and 2b.

Figure 3:
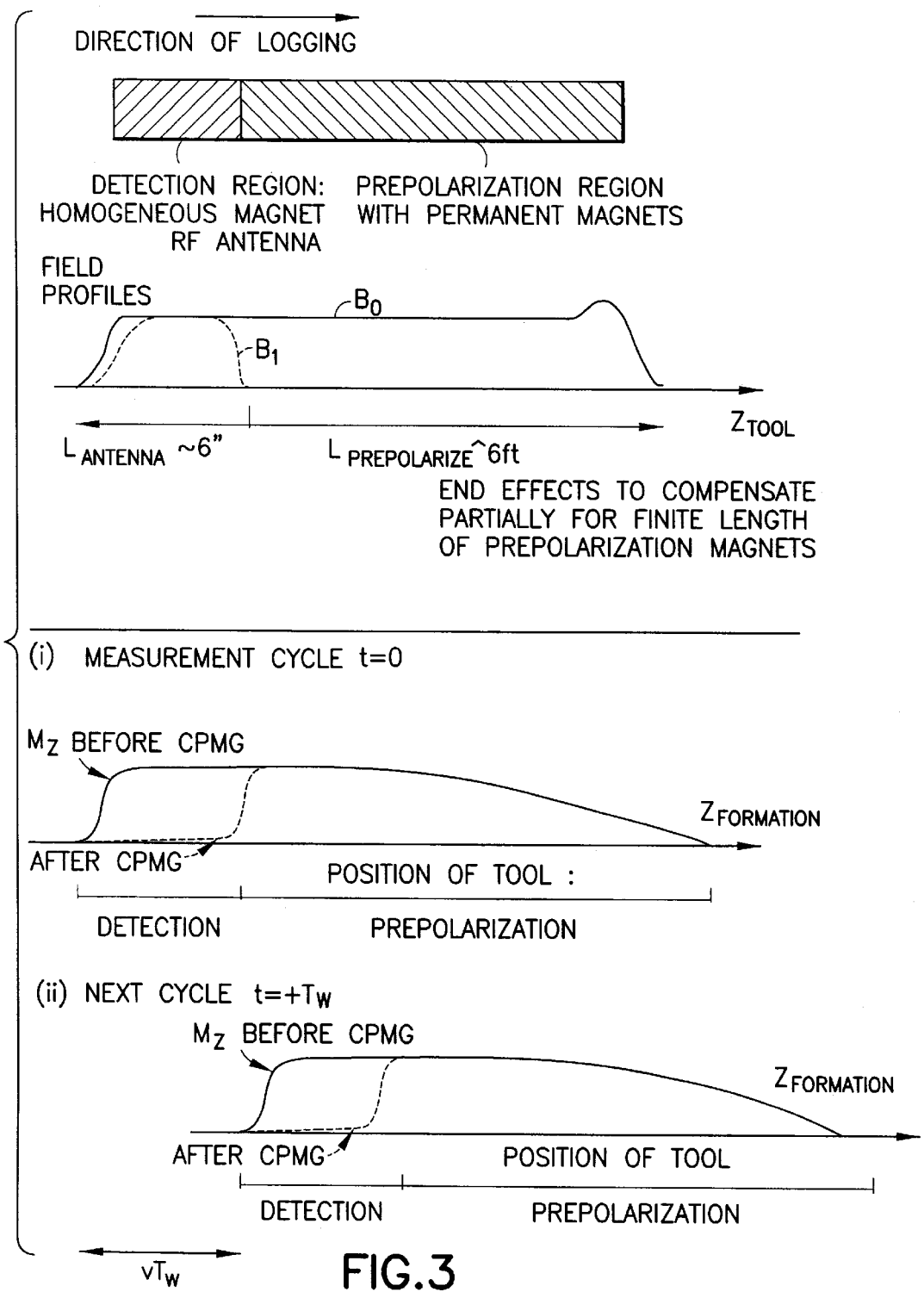
FIG. 3 illustrates a schematic, sequence diagram of the field and magnetization profile of an NMR tool of this invention.

FIG. 3, Top is a schematic drawing of some of the essential features of an NMR logging tool and schematic drawing of the magnetic fields $B_0$ and $B_1$ as a function of position along the tool. The tool consists of a 'detection region', and located next to it in the direction of logging a 'prepolarization region'. The detection region produces a homogeneous magnetic field in the formation and includes an antenna and electronic circuitry (not shown) that is used to excite the spins and detect the weak NMR signal. The prepolarization region produces a magnetic field in the formation.

The extent of the detection region is determined by the strength of the rf field $B_1$, (indicated by the dashed line) and by the $B_0$ homogeneity in the antenna region. The homogeneity of $B_0$ in the prepolarization region is not that critical. In fact, it can be advantageous to decrease the field homogeneity above the detection region to yield a sharper definition of the sensitive zone. At the top end, the field $B_0$ is shown to increase before it is reduced to zero, to compensate somewhat for the finite length of the prepolarization region.

FIG. 3, Bottom shows longitudinal magnetization versus position in the formation for two measuring cycles. The location of the tool is indicated below the graphs. Magnetization ahead of the tool is essentially zero. The magnetic field of the prepolarization region is polarizing the formation, leading to full polarization in front of the detection region (solid curve). The measured amplitude of the NMR measurement is proportional to the longitudinal magnetization. After the CPMG sequence, the longitudinal magnetization in front of the detection region is reduced close to zero (dashed curve). The next measurement cycle is performed after the tool has been moved a distance $vT_w$ that is equal to the length of the detection region.

NMR well logging can be used for determining properties of earth formations and properties of the fluid filling the pore space of the formation. These properties include the fractional volume of pore space, $\phi$, the fractional volume of mobile fluid filling the pore spaces of the earth formations, pore size distributions, viscosity and diffusion coefficient of fluids.

NMR is based on the fact that the nuclei of many elements have angular momentum ('spin') and a magnetic moment. The nuclear spins align themselves along an externally applied static field, $B_0$, with a relaxation time that is called $T_1$, the so-called spin-lattice relaxation time. The equilibrium situation can be disturbed by a pulse of an oscillating rf magnetic field, $B_1$, which tips the spins away from the static field direction. The angle through which the spins are tipped depends on the amplitude and duration of the rf field.

After tipping, the spins precess around the static field at a particular frequency (i.e. the Larmor frequency), given by $\omega_0 = \gamma B_0$, where $B_0$ is the strength of the static field and $\gamma$ is the gyromagnetic ratio, a nuclear constant. For hydrogen, $\gamma/2\pi = 4258$ Hz/Gauss. The precessing magnetization is detected with the antenna. If the spins are initially in thermal equilibrium, the amplitude of the signal immediately after the rf pulse is proportional to the number of nuclei in the formation. Using hydrogen NMR, this measurement can be translated into porosity $\phi$, if the hydrogen index of the fluid is known.

The precessing signal decays with a time constant $T_2^*$. Inhomogeneities in the static field lead to slightly different precessing frequencies in different parts of the formation, thus leading to a rapid dephasing of the signal. The effects of this dephasing can be removed by a technique called spin-echo measurements.

In spin echo measurements, a series of rf pulses is applied. The first pulse is commonly adjusted to lead to a nominal 90° tipping angle. This so-called 90° pulse causes the spins to start precessing. Then a one hundred eighty degree pulse is applied to keep the spins in the measurement plane, but to cause the spins which are dispersing in the transverse plane to reverse direction and to refocus. By repeatedly reversing the spins by one hundred eighty degree pulses, a series of 'spin echoes' appear. This succession of one hundred and eighty degree pulses after an initial ninety degree pulses is the Carr-Purcell sequence. Meiboom and Gill devised a modification to the Carr-Purcell pulse sequence such that after the spins are tipped by ninety degrees and start to dephase, the carrier of the one hundred eighty degree pulses is phase shifted relative to the carrier of the ninety degree pulse. This is the so-called CPMG pulse sequence. The decay time of the echo amplitude is called the spin-spin relaxation time $T_2$.

The parameters $T_1$ and $T_2$ are sensitive to the molecular environment and are important formation evaluation parameters. Information on diffusion effects can be obtained by varying the spacing between the 180 degree pulses, $t_E$.

In rocks, spins in different pores or different fluid phases have different relaxation times $T_1$ and $T_2$ As a consequence, the signal decay can in general not be described by a single exponential. A distribution, $f(T_2)$, is required to characterize the full decay. (See for example the discussion on distributions in U.S. Pat. No. 5,486,762 by Freedman et al.).

It is a common practice to alternate the phase of the first 90 pulse by 180 degrees for subsequent measurements. This process of phase cycling helps to eliminate systematic offsets.

In U.S. Pat. No. 5,055,787, issued on Oct. 8, 1991 and assigned to Kleinberg et al., a prepolarization magnet has been already discussed. It is stated that the field of the prepolarization magnet should be preferably much stronger than the magnetic field in the sensitive zone. This ensures that the detected NMR signal of the formation is as large as possible One disadvantage of this implementation is that although the amplitude of the NMR signal is increased, it depends in general not only on the porosity of the formation, but it depends also strongly on the longitudinal relaxation $T_1$, the wait time $T_w$ and the logging speed, v. This makes it difficult to extract the correct porosity of the formation from the NMR measurements.

In the present invention, we are concerned that the porosity and bound fluid can be extracted directly from the signal, without requiring additional measurements. It minimizes the effects of $T_1$, $T_w$, and v by combining a particular prepolarization magnet with a pulse sequence adapted to the tool dimensions and logging speed. As explained above, the prepolarization magnets are chosen to be as long as practically possible. The field of the prepolarization magnets should essentially match the field at the sensitive zone. In order to take advantage of the long prepolarization magnets for reliable porosity logging, it is also essential to chose the correct wait time $T_w$. It is chosen such that subsequent measurements interrogate non-overlapping parts of the formation, i.e. $T_w = L_{antenna}/v$.

In the prior art NMR method of measuring porosity, the longitudinal magnetization of the spins vanishes, after the CPMG measurement. The spins assume the equilibrium magnetization $M_0$ with the time constant $T_1$:

$$M_z(t) = M_0(1 - \exp\{-t/T_1\}) \qquad (1)$$

Here t is the time after the end of the CPMG sequence. The NMR porosity is derived from the initial amplitude of the signal, which is proportional to the longitudinal magnetization just prior to the CPMG sequence. The initial amplitude is simply proportional to the NMR porosity, or more precisely, the number of hydrogen nuclei in the formation, when the wait time is long enough, and all the spins have acquired thermal equilibrium $M_0$. However, if the formation contains fluids with very long relaxation time $T_1$, the wait time $T_w$ in practical logging operations is often insufficient to fully polarize all the spins. The measured NMR porosity is then reduced from the true porosity by a factor of $(1-\exp\{-t_w/T_1\})$. In order to correct for this polarization factor, and extract the correct porosity, the $T_1$ distribution of the formation has to be known.

In current practice, the $T_1$ distribution is estimated from the measured $T_2$ decay, assuming that the relaxation times $T_1$ are simply related to $T_2$ by a constant factor, typically in the range between 1.5 and 3.

There are several simplifications and omissions in the current procedure that make the extraction of the NMR porosity highly problematical, if the polarization factor deviates significantly from 1. This occurs in formations with light hydrocarbons, gas, vuggy carbonates, or when higher logging speeds are used.

For fluids with long relaxation times $T_1$, it is, in general, not possible to estimate $T_1$ from the measured CPMG decay times $T_2$. The measured $T_2$, but not $T_1$, is affected by diffusion in the inhomogeneous magnetic fields of the tool. In addition, tool motion can lead to additional signal decay. This effect is especially important for fluids with high diffusion coefficients and long bulk relaxation times. In general, the true relaxation times $T_1$ are underestimated.

In addition, the polarization correction given in Equation 1 is only correct for a stationary tool. Spins are moved in front of the antenna that have not been previously saturated by the rf pulses, when a tool is moving. This is most pronounced, when $vT_w$ (v is the logging speed) becomes comparable, or larger than the length of the antenna. In general, the correction is smaller than predicted by Equation 1, except for large logging speeds.

As a consequence of these complications, the polarization corrections applied to the present logging tools are unreliable. In general, there is not enough information contained in the data of a single logging pass to infer the correct porosity when fluids with long $T_1$ are present. In practice, the log analyst will adjust the ratio of the input parameter $T_1/T_2$ until a reasonable result is obtained.

One prior art approach for overcoming these limitations, was to use a station stop and very long wait times to insure that all the spins were completely polarized. This approach was not always practical.

Alternatively, a multiple wait time logging pass, was used, where the wait time $T_w$ was changed. In principle, it was possible to infer $T_1$ and $T_2$ of the formation from this extra information.

A Logging Tool to Measure NMR Porosity at up to 1800 ft./hr., or even more

In order to minimize the polarization correction, the spins in front of the antenna must be fully polarized, when making a CPMG measurement. There are two conditions that have to be fulfilled:

1. The spins have to be exposed to the magnetic field $B_0$ for a time long enough relative to the relaxation time $T_1$.
2. The spins must not have been saturated by rf fields from a previous CPMG measurement sequence, during a time long enough relative to $T_1$.

The tool designed for this invention uses the advantage of the tool motion to measure every spin in the formation only once. In this manner, the wait time is not limited by the longest value of $T_1$, and it becomes possible to log a formation (with long relaxation times) at a relatively high logging speed, and a relatively short wait time, e.g., v=1800 ft./hr.; $T_w$=1 s. The tool requirements for an NMR porosity tool that will fit this situation, becomes an instrument having a longer prepolarization region and a short antenna.

The first requirement implies that the tool has to have a prepolarization region above the antenna, that is longer than $vT_{1,max}$, where v is the logging speed, and $T_{1,max}$ is the longest relaxation time encountered. More precisely, the longitudinal polarization for a spin exposed to the time dependent magnetic field $B_0(t)$ is given by:

$$M_z(r) = \frac{x}{\mu_0} \cdot \frac{1}{T_1} \int_0^\infty dt \exp\{-t/T_1\} B_0(r+vt) \quad (2)$$

Using a logging speed of 1800 ft./hr.=6 in./s., a prepolarization region of 6 feet polarizes all the spins with $T_1 \leq 5$ s to at least 90% of $M_0$. This is a realistic/conservative specification. In this example, the spins are exposed to the field $B_0$ for at least 12 seconds.

This estimate assumes a constant profile of $B_0$ over the prepolarization region. It is possible to improve the performance for long $T_1$ by increasing the field strength at the upper end to partially compensate for the finite length of the prepolarization region.

At first impression, the second above requirement, implies that the wait time $T_w$ has to be large compared to $T_{1,max}$. This is not correct for a moving tool. Only the spins in front of the antenna must not have been recently saturated. It implies that the antenna should be no longer than $vT_w$. For a logging speed of 1800 ft./hr., and the antenna of the tool (6" length), the wait time can be as short as one second. During this wait time, all the spins that have been excited (and saturated) by the previous CPMC sequence, have left the region in front of the antenna and have been replaced by "fresh" spins that have not been affected by previous rf radiation. For this logging speed, increasing the wait time $T_w$ does not serve any useful purpose. In reality, it would leave some of the formation unexplored. Ideally, the wait time should be adjusted according to the logging speed, such that $vT_w$, the tool movement during the wait time, is a constant equal to the effective antenna length. This corresponds to depth logging, rather than time logging.

Referring to FIG. 3, a schematic diagram of the porosity profile for the NMR tools of this invention, is shown.

Homogeneity of Prepolarization Region

The required homogeneity of the magnets in the prepolarization region is lower than those in the sensitive zone, where the homogeneity has to be better than $B_1$, the rf strength. It is estimated, that homogeneities in the range of a few percent to 10% should be adequate. In addition, it is not critical that there be a dead zone close to the borehole in the prepolarization region.

Power requirements of the tool shown in FIG. 3, does not increase compared to conventional tools, because the sensitive zone has the same volume. The weight of the tool will increase, because additional magnets are required. This is estimated to be approximately 100 kg.

Tool motion with a short antenna causes extra signal decay and will distort the shape (but not the area) of the $T_2$ distribution. However, the most important NMR products are not affected, viz. bound fluid porosity and free fluid porosity and the permeability estimate based on the Timur expression, $\phi^4/S_{wi}^2$, where $\phi$ is the porosity and $S_{wi}$ is the irreducible water saturation.

Clearly, the signal cannot last longer than $L_{antenna}/v$, where L is the length of the antenna. $L_{antenna}/v$ should be comparable to the wait time. In current tools, the signal actually decays somewhat faster than $L_{antenna}/v$, because end effects bend the sensitive region. In fact, a long prepolarization region will, in general, help to straighten the sensitive region.

The measured $T_2$ distribution will be distorted at the long relaxation times, but the area under the curve will be preserved. Given the tool geometry and the logging speed, correction can be made for these predictable effects (limited by the available signal to noise ratio). The exact shape of the $T_2$ distribution at long times, is not as critical as that for current NMR tools, because the usual polarization correction is not made.

It should also be understood, that in current logging tools, the shape of the $T_2$ distribution for long times is already affected by diffusion and speed effects. The distribution will not be distorted at the short end. In particular, the bound fluid porosity will be unaffected. The motion effect can be reduced by constructing a more complicated, segmented antenna that extends further along the tool length.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. An instrument for obtaining NMR measurements in a well logging formations, comprising:
   an extended prepolarization region, said extended prepolarization region having means for sufficiently polarizing said well logging formations ahead of a detection region at motion speeds exceeding 300 feet per hour; and
   a substantially shorter detection region relative to, said extended prepolarization region, said detection region having wait times between successive NMR measurements such that there is no overlap in the portions of the formation subjected to successive measurements.

2. The instrument for obtaining NMR measurements in accordance with claim 1, wherein said wait time is substantially equal to the length of said detector region divided by the motion speed of the instrument.

3. The instrument for obtaining NMR measurements in accordance with claim 1, wherein said instrument has a maximal resolution of about one foot.

4. The instrument for obtaining NMR measurements in accordance with claim 1, wherein said instrument has a preferred motion speed of approximately 1,800 feet per hour.

5. The instrument for obtaining NMR measurements in accordance with claim 1, wherein said detection region comprises homogeneous magnets and rf antenna, and said prepolarization region comprises permanent magnets.

6. The instrument for obtaining NMR measurements in accordance with claim 5, wherein said rf antenna is adapted to detect multiple rf frequencies, and said detection region has wait times between successive NMR measurements at any particular frequency such that there is no overlap in the portions of the formation subject to successive measurement at said frequency.

7. The instrument for obtaining NMR measurements in accordance with claim 1, wherein said detection region has preferred wait times between successive NMR porosity measurements of approximately one second at said motion speed.

8. The instrument for obtaining NMR measurements in accordance with claim 1, wherein the length of the prepolarizing region is at least as long as the speed of the tool multiplied by the maximum $T_1$ expected to be encountered in the formation.

9. A method of making NMR measurements in a formation surrounding a borehole, with a tool having a prepolarization region and a detection region, comprising:

magnetically prepolarizing a portion of the formation with said prepolarizing region of the tool;

moving the tool so as to bring the detection region adjacent a part of the prepolarized portion of the formation;

making an NMR measurement with said detection region;

moving the tool in the same direction so as to extend the prepolarization of the formation and to bring the detection region of the tool adjacent to the next part of the prepolarized portion; and making another NMR measurement after a wait time so that there is no overlap between the successive detection portions of the formation.

10. A method according to claim 9, wherein the wait time, designated $T_w$, is substantially equal to $L_{antenna}/v$, where $L_{antenna}$ is substantially equal to the length of said detection region, and v is the speed at which the tool is moved through the formation.

11. A method according to claim 9, wherein any given part of the formation is subjected to only one NMR measurement so that said measurement is substantially not affected by any previous measurements.

12. A method according to claim 9 wherein the length of the prepolarizing region is at least as long as the speed of the tool multiplied by the maximum $T_1$ expected to be encountered in the formation.

13. A method according to claim 9, wherein the tool is moved with a speed such that the prepolarizing region is at least as long as the speed of the tool multiplied by the maximum $T_1$ expected to be encountered in the formation.

14. A method according to claim 9, wherein saids NMR measurements are made at multiple rf frequencies, and the wait time is chosen for any particular frequency such that there is no overlap between successive detection portions of the formation at said frequency.

* * * * *